(12) United States Patent
Shermer et al.

(10) Patent No.: US 10,835,681 B2
(45) Date of Patent: Nov. 17, 2020

(54) TIME-OF-USE ACTIVATED SYRINGE STOPPER

(71) Applicant: Becton, Dickinson and Company, Franklin Lakes, NJ (US)

(72) Inventors: Charles D. Shermer, Raleigh, NC (US); Qihua Xu, Cary, NC (US); Christopher DeMaria, Morrisville, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 532 days.

(21) Appl. No.: 15/556,917

(22) PCT Filed: Mar. 17, 2016

(86) PCT No.: PCT/US2016/022837
§ 371 (c)(1),
(2) Date: Sep. 8, 2017

(87) PCT Pub. No.: WO2016/153912
PCT Pub. Date: Sep. 29, 2016

(65) Prior Publication Data
US 2018/0056006 A1    Mar. 1, 2018

Related U.S. Application Data

(60) Provisional application No. 62/137,369, filed on Mar. 24, 2015.

(51) Int. Cl.
*A61M 5/315*    (2006.01)
*A61M 5/31*    (2006.01)

(52) U.S. Cl.
CPC ...... *A61M 5/31513* (2013.01); *A61M 5/3129* (2013.01); *A61M 5/31565* (2013.01);
(Continued)

(58) Field of Classification Search
CPC .......... A61M 2005/31521; A61M 2205/0216; A61M 2205/0222; A61M 2207/00; A61M 5/3129; A61M 5/31513; A61M 5/31565
See application file for complete search history.

(56) References Cited

U.S. PATENT DOCUMENTS 2,895,773 A    7/1959  McConnaughey
3,831,601 A    8/1974  Kessell
(Continued)

FOREIGN PATENT DOCUMENTS

DE    2514412 A1    10/1976
FR    1500009 A    11/1967
(Continued)

*Primary Examiner* — Bradley J Osinski
(74) *Attorney, Agent, or Firm* — The Webb Law Firm (57) ABSTRACT

A time-of-use activated syringe assembly includes a syringe barrel defining a chamber, a plunger rod having a forward attachment end located within the chamber of the barrel, and a stopper located within the chamber of the barrel and including a rearward end adapted to receive the plunger rod. The stopper includes a first perimetrical skirt extending around an outer circumference thereof and extending toward a front end of the stopper. An activation mechanism is associated with at least one of the stopper and the plunger rod, and the plunger rod is configured for transition between a pre-loaded position in which the activation mechanism is unactivated and a loaded position in which the activation mechanism is activated. Upon activation, the activation mechanism applies a radial force to the first perimetrical skirt causing the skirt to seal against an inner wall of the syringe barrel.

19 Claims, 6 Drawing Sheets

(52) U.S. Cl.
CPC .............. *A61M 2005/31521* (2013.01); *A61M 2205/0216* (2013.01); *A61M 2205/0222* (2013.01); *A61M 2207/00* (2013.01)

(56) References Cited

U.S. PATENT DOCUMENTS

| | | | |
|---|---|---|---|
| 3,939,833 | A | 2/1976 | Hansson et al. |
| 4,180,069 | A | 12/1979 | Walters |
| 4,215,701 | A | 8/1980 | Raitto |
| 4,266,557 | A * | 5/1981 | Merry ............... A61M 5/31513 600/576 |
| 4,500,310 | A | 2/1985 | Christinger |
| 4,543,093 | A | 9/1985 | Christinger |
| 5,735,825 | A | 4/1998 | Stevens et al. |
| 7,749,202 | B2 | 7/2010 | Miller et al. |
| 7,819,845 | B2 | 10/2010 | Cude |
| 9,289,557 | B2 | 3/2016 | Ivosevic et al. |
| 9,642,969 | B2 | 5/2017 | Ivosevic et al. |
| 2011/0034882 | A1 | 2/2011 | Quinn et al. |
| 2012/0253291 | A1 | 10/2012 | Ivosevic et al. |
| 2012/0253292 | A1 | 10/2012 | Ivosevic et al. |
| 2017/0203045 | A1 | 7/2017 | Ivosevic et al. |

FOREIGN PATENT DOCUMENTS

| | | |
|---|---|---|
| GB | 1260103 | 1/1972 |
| WO | 8500524 A1 | 2/1985 |

* cited by examiner

TIME-OF-USE ACTIVATED SYRINGE STOPPER

CROSS REFERENCE TO RELATED APPLICATIONS

This application is a National Stage of International Patent Application No. PCT/US2016/022837, filed on Mar. 17, 2016, which claims priority to United States Provisional Application Ser. No. 62/137,369, filed Mar. 24, 2015, each of which is hereby incorporated by reference in its entirety.

BACKGROUND OF THE INVENTION

Field of the Invention

The present disclosure relates generally to a stopper for use with a syringe and, more particularly, the present disclosure relates to a stopper which is activated at the time of use of the syringe to create a seal between the stopper and the barrel of the syringe.

Description of Related Art

A typical syringe assembly consists of a cylindrical barrel having an access opening formed at a proximal end and a smaller discharge opening formed at an opposite or distal end. The proximal end is adapted to receive a stopper and a plunger rod assembly. The stopper is designed to snugly seal against an interior surface of the barrel. A needle, a threaded member, or a non-threaded member is usually attached to the discharge opening on the barrel. The needle can be used to penetrate a surface while the threaded member can be used to attach the syringe to another medical device, such as a catheter. One of the purposes of the stopper is to provide a relatively air tight seal between itself and the syringe barrel so that movement of the stopper within the barrel will cause fluid, such as liquid medication, biological samples, or blood, to be drawn into or forced out of the syringe through the discharge opening. The stopper should be sufficiently flexible so that it will seal the inside diameter of the barrel without requiring excessive force to move it within the barrel.

Conventional syringe systems are designed with the stopper outer diameter and barrel inner diameter interface having significant interferences. This degree of interference is needed to create and maintain an adequate fluid/air seal for functional filling and injection operations over the entire intended shelf-life of the system. As a result of this configuration, the interface of the stopper and the syringe barrel maintains, at all times, a sealing pressure capable of withstanding the challenges of filling and injecting even though this magnitude of sealing pressure is not required when the syringe is not in use.

This interface between the stopper and the barrel can result in high compression/deformation of the stopper and barrel, and high contact forces of the stopper against the inner wall of the barrel, both of which can lead to undesired effects such as: (1) compression set or cold flow of the stopper and barrel where the outer diameter of the stopper or wall of the barrel take a permanent deformation and the effective seal between the stopper and barrel is lost; (2) potential degradation of the stopper material during storage resulting in contamination of the syringe contents; (3) high hand forces required to initially move the stopper after an extended storage period, often referred to as "break-loose" or "break-out" forces; (4) high hand forces required to advance the stopper during an injection, often referred to as "sustaining" forces; and (5) high oscillating forces while advancing the stopper during an injection, often referred to as "sticktion" forces. It has been found that sticktion can cause a syringe system to perform poorly in a syringe pump application, where high accuracy of desired flow rate over an extended period is required.

Also, because the passive contact pressure between the stopper and the syringe barrel wall can be as high as approximately 300 psi or more, the syringe barrel can require a relatively large barrel wall thickness in order to prevent localized barrel creep or bulging during the shelf life. Also, because of high contact forces and high friction coefficient between current elastomeric or rubber stoppers and the inner wall of the barrels, currently, syringe designs often include the use of a liquid lubricant such as silicone oil to reduce the break-loose or break-out hand forces required to operate the syringe.

Some of the problems discussed above have been alleviated by the use of plastic stoppers formed from a rigid or semi-rigid polymeric material having an elastic modulus in the range of about 0.01 GPa to about 5 GPa. These stoppers rely on the use of fluid pressure during an injection process to cause the stopper to seal against the interior surface of a syringe barrel. Because the stopper is designed to seal upon the application of fluid pressure, the stopper works well in high pressure applications, but does not work as well when used in low pressure applications.

There is a need in the art for a stopper that also functions well in low injection pressure applications to produce a leak-free seal. There is also a need in the art for a stopper/plunger rod arrangement that works well with stoppers formed from a variety of plastic and elastomeric materials, including bio-based elastomers, which have higher durometer/compression set material characteristics. There is yet another need in the art for a stopper/plunger rod arrangement that reduces the need to "fine-tune" the design of the seal contact pressures/stresses/strains which initiate at assembly and then vary due to the eventual material creep of both the syringe barrel and stopper across an anticipated shelf-life.

SUMMARY OF THE INVENTION

The present invention is directed to a stopper/plunger rod arrangement that overcomes the disadvantages discussed above, does not require the use of a lubricant, works well in both high and low pressure injection applications, can be manufactured with wider tolerances and still maintain its sealing function, has a higher percentage of acceptable parts in production, reduces the amount of scrap produced, and consequently reduces the costs of manufacture.

In accordance with an embodiment of the invention, a stopper adapted for attachment with a plunger rod for use within a syringe barrel includes a main body defining an open rearward end and a closed front end. The open rearward end is adapted to receive a forward front attachment end of the plunger rod. The stopper also includes a first perimetrical skirt extending around an outer circumference of the main body toward the closed front end of the main body portion. An activation mechanism is associated with at least one of the stopper and the plunger rod. The plunger rod is configured for transition between a pre-loaded position in which the activation mechanism is unactivated and a loaded, ready-to-use position in which the activation mechanism is activated so that it applies a radial force to the first perimetrical skirt causing the first perimetrical skirt to seal against an inner wall of the syringe barrel.

According to one design, the activation mechanism can include a first engagement member extending around an inner circumference of the stopper main body and a second engagement member extending around an outer circumference of the forward front attachment end of the plunger rod. The first and second engagement members become engaged with one another upon transition of the plunger rod from the pre-loaded position to the loaded, ready-to-use position. The first engagement member can include a notch and the second engagement member can include a protrusion. Alternatively, the first engagement member can include a protrusion and the second engagement member can include a notch.

According to another design, the activation mechanism can include a flexing collet or basket associated with the plunger rod, wherein the flexing collet or basket is configured for expanding and locking in place to apply the radial force to the first perimetrical skirt upon transition of the plunger rod from the pre-loaded position to the loaded, ready-to-use position.

According to still another design, the activation mechanism can include a collapsing sliding wedge associated with the plunger rod, wherein the collapsing sliding wedge is configured for expanding and locking in place to apply the radial force to the first perimetrical skirt upon transition of the plunger rod from the pre-loaded position to the loaded, ready-to-use position.

According to yet another design, the activation mechanism can include a camming mechanism associated with the stopper and the plunger rod, and wherein activation of the camming mechanism applies the radial force to the first perimetrical skirt upon transition of the plunger rod from the pre-loaded position to the loaded, ready-to-use position.

The stopper can further include a second perimetrical skirt extending around an outer circumference of the main body toward the open rearward end of the main body and activation of the activation mechanism applies the radial force to at least both the first and the second perimetrical skirts to cause at least the first and second perimetrical skirts to seal against the inner wall of the syringe barrel.

The stopper can be formed from a bio-based or partial bio-based polymer material. The stopper can also have a durometer of hardness between Shore D 30-60.

The rearward end of the stopper is configured to cooperate with the forward front attachment end of the plunger rod to engage the forward front attachment end of the plunger rod in the pre-loaded position and to guide the forward front attachment end of the plunger rod into the stopper during transition from the pre-loaded position to the loaded position.

In accordance with another embodiment, a plunger rod and stopper assembly adapted for use with a syringe barrel includes a plunger rod having a forward front attachment end and a back end and extending along a longitudinal axis. The assembly further includes a stopper having a main body defining an open rearward end and a closed front end. The open rearward end is adapted to receive the forward front attachment end of the plunger rod. The stopper also includes a first perimetrical skirt extending around an outer circumference of the main body toward the closed front end of the main body portion. The assembly also includes an activation mechanism associated with at least one of the stopper and the plunger rod, wherein the plunger rod is configured for transition between a pre-loaded position in which the activation mechanism is unactivated and a loaded, ready-to-use position in which the activation mechanism is activated and applies a radial force to the first perimetrical skirt causing the first perimetrical skirt to seal against an inner wall of the syringe barrel.

According to one design, the first engagement member can be one of a notch or a protrusion and the second engagement member can be the opposite of the notch or protrusion of the first engagement member.

According to another design, the activation mechanism can include a flexing collet or basket associated with the plunger rod. The flexing collet or basket is configured for expanding and locking in place to apply the radial force to the first perimetrical skirt upon transition of the plunger rod from the pre-loaded position to the loaded, ready-to-use position.

According to yet another design, the activation mechanism can include a collapsing sliding wedge associated with the plunger rod configured for expanding and locking in place to apply the radial force to the first perimetrical skirt upon transition of the plunger rod from the pre-loaded position to the loaded, ready-to-use position.

According to still yet another design, the activation mechanism can include a camming mechanism associated with the stopper and the plunger rod, wherein activation of the camming mechanism applies the radial force to the first perimetrical skirt upon transition of the plunger rod from the pre-loaded position to the loaded, ready-to-use position.

According to another embodiment of the invention, a time-of-use activated syringe assembly includes a syringe barrel defining an interior chamber, a proximal end, and a distal end terminating in a tip having an opening extending therethrough; a plunger rod having a forward front attachment end and a back end, and extending along a longitudinal axis, wherein the forward front attachment end is located within the interior chamber of the syringe barrel; and a stopper located within the interior chamber of the syringe barrel, the stopper having a main body defining an open rearward end and a closed front end, wherein the open rearward end is adapted to receive the forward front attachment end of the plunger rod. The stopper includes a first perimetrical skirt extending around an outer circumference of the main body toward the closed front end of the main body portion. The syringe assembly also includes an activation mechanism associated with at least one of the stopper and the plunger rod, wherein the plunger rod is configured for transition between a pre-loaded position in which the activation mechanism is unactivated and a loaded, ready-to-use position in which the activation mechanism is activated and applies a radial force to the first perimetrical skirt causing the first perimetrical skirt to seal against an inner wall of the syringe barrel.

The syringe assembly can include a second perimetrical skirt extending around an outer circumference of the main body toward the open rearward end of the main body and activation of the activation mechanism applies the radial force to at least both the first and the second perimetrical skirts to cause at least the first and second perimetrical skirts to seal against the inner wall of the syringe barrel.

The rearward end of the stopper can be configured to cooperate with the forward front attachment end of the plunger rod to engage the forward front attachment end of the plunger rod in the pre-loaded position and to guide the forward front attachment end of the plunger rod into the stopper during transition from the pre-loaded position to the loaded position.

The syringe assembly can also include a retaining ring at the proximal end of the syringe barrel extending toward the interior chamber of the syringe barrel and a stop member associated with the plunger rod. The stop member can be located proximal to the stopper. The retaining ring and the stop member cooperate together to prevent the plunger rod from inadvertently separating from the syringe barrel.

In accordance with another embodiment of the invention, a method of activating a stopper within a syringe barrel includes providing a stopper within a syringe barrel, the stopper having a main body defining an open rearward end and a closed front end, and wherein the stopper includes a first perimetrical skirt extending around an outer circumference of the main body toward the closed front end of the main body portion; providing a plunger rod having a forward front attachment end and a back end and extending along a longitudinal axis; and providing an activation mechanism on at least one of the stopper and the plunger rod. The method further includes associating the forward front attachment end of the plunger rod with one of the syringe barrel and the open rearward end of the stopper in a pre-loaded position and transitioning the plunger rod from the pre-loaded position in which the activation mechanism is unactivated to a loaded, ready-to-use position in which the activation mechanism is activated and applies a radial force to the first perimetrical skirt causing the first perimetrical skirt to seal against an inner wall of the syringe barrel. Transitioning of the plunger rod from the pre-loaded position to the loaded, ready-to-use position includes applying a force to the plunger rod to cause the forward front attachment end of the plunger rod to enter into the open rearward end of the stopper. According to one embodiment, this force can be a distally directed force.

In accordance with still another embodiment of the invention, a method of activating a time-of-use syringe assembly includes providing a syringe barrel defining an interior chamber, a proximal end, and a distal end terminating in a tip having an opening extending therethrough, providing a stopper within the syringe barrel, the stopper having a main body defining an open rearward end and a closed front end, the stopper including a first perimetrical skirt extending around an outer circumference of the main body toward the closed front end of the main body portion, providing a plunger rod having a forward front attachment end and a back end and extending along a longitudinal axis, providing an activation mechanism on at least one of the stopper and the plunger rod, associating the forward front attachment end of the plunger rod with the syringe barrel and the open rearward end of the stopper in a pre-loaded position, and transitioning the plunger rod from the pre-loaded position in which the activation mechanism is unactivated to a loaded, ready-to-use position in which the activation mechanism is activated and applies a radial force to the first perimetrical skirt causing the first perimetrical skirt to seal against an inner wall of the syringe barrel. Transitioning of the plunger rod from the pre-loaded position to the loaded, ready-to-use position includes applying a force to the plunger rod to cause the forward front attachment end of the plunger rod to enter into the open rearward end of the stopper. According to one embodiment, the force applied to the plunger rod can be a distally directed force. The method can further include providing a retaining ring at the proximal end of the syringe barrel extending toward the interior chamber of the syringe barrel and providing a stop member on the plunger rod. The stop member can be located proximal to the stopper and the retaining ring and the stop member are configured to cooperate together to prevent the plunger rod from inadvertently separating from the syringe barrel when the plunger rod is in the pre-loaded position.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

Corresponding reference characters indicate corresponding parts throughout the several views. The exemplifications set out herein illustrate exemplary embodiments of the disclosure, and such exemplifications are not to be construed as limiting the scope of the disclosure in any manner.

DESCRIPTION OF THE INVENTION

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Figure 1:
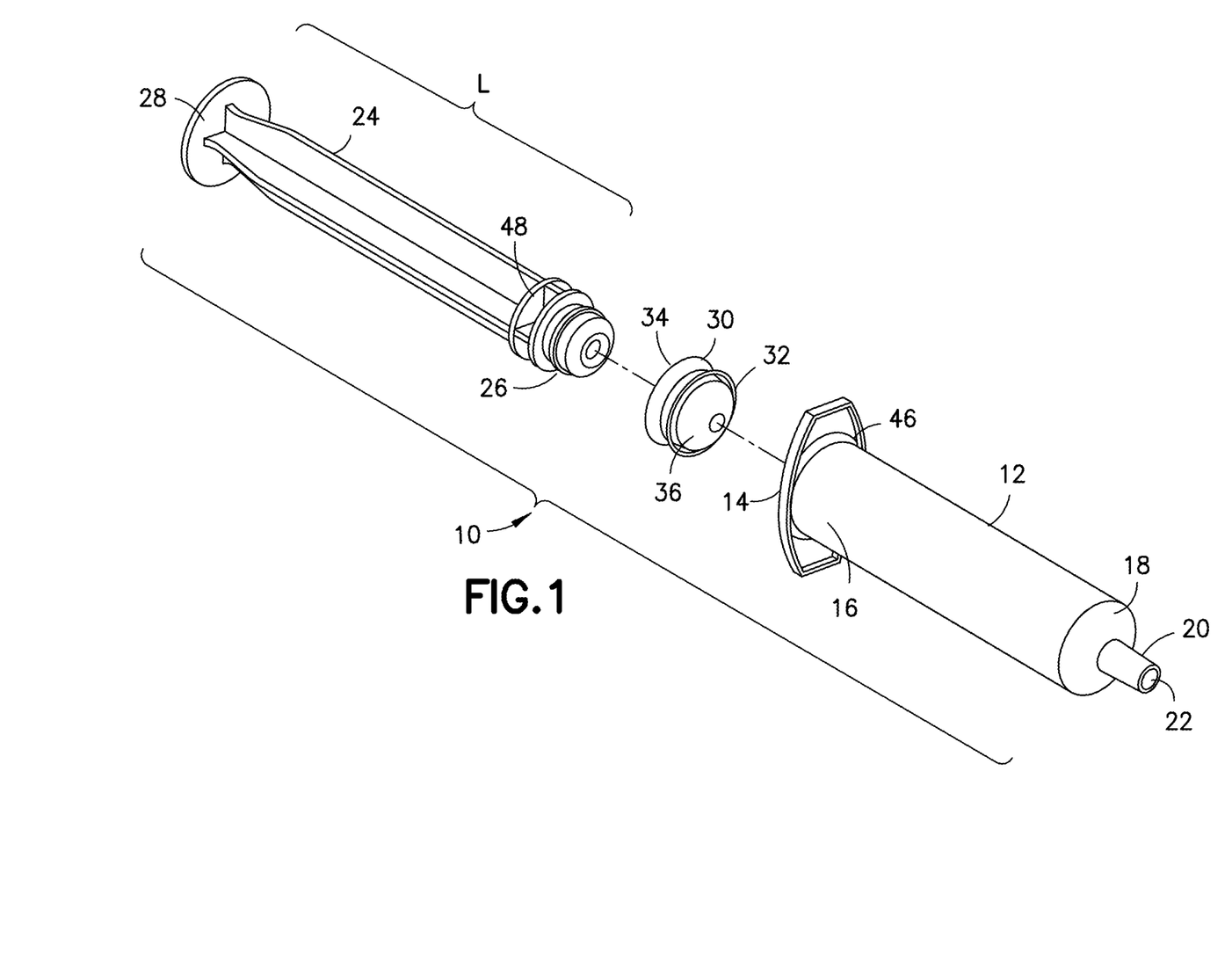
FIG. 1 is an exploded perspective view of a time-of-use activated syringe assembly in accordance with an embodiment of the present invention.

Reference is now made to FIG. 1 which shows an exploded perspective view of a time-of-use activated syringe assembly, generally indicated as 10, in accordance with an embodiment of the present invention. The time-of-use, activated syringe assembly 10 includes a syringe barrel 12 defining an interior chamber 14, a proximal end 16, and a distal end 18 terminating in a tip 20 having an opening 22 extending therethrough. The syringe assembly 10 also includes a plunger rod 24 having a forward front attachment end 26 and a back end 28 and extending along a longitudinal axis "L". When assembled, the forward front attachment end 26 is located within the interior chamber 14 of the syringe barrel 12. A stopper 30 is located within the interior chamber 14 of the syringe barrel 12. The stopper 30 has a main body 32 defining an open rearward end 34 and a closed front end 36. The open rearward end 34 is adapted to receive the forward front attachment end 26 of the plunger rod 24.

Figure 2:
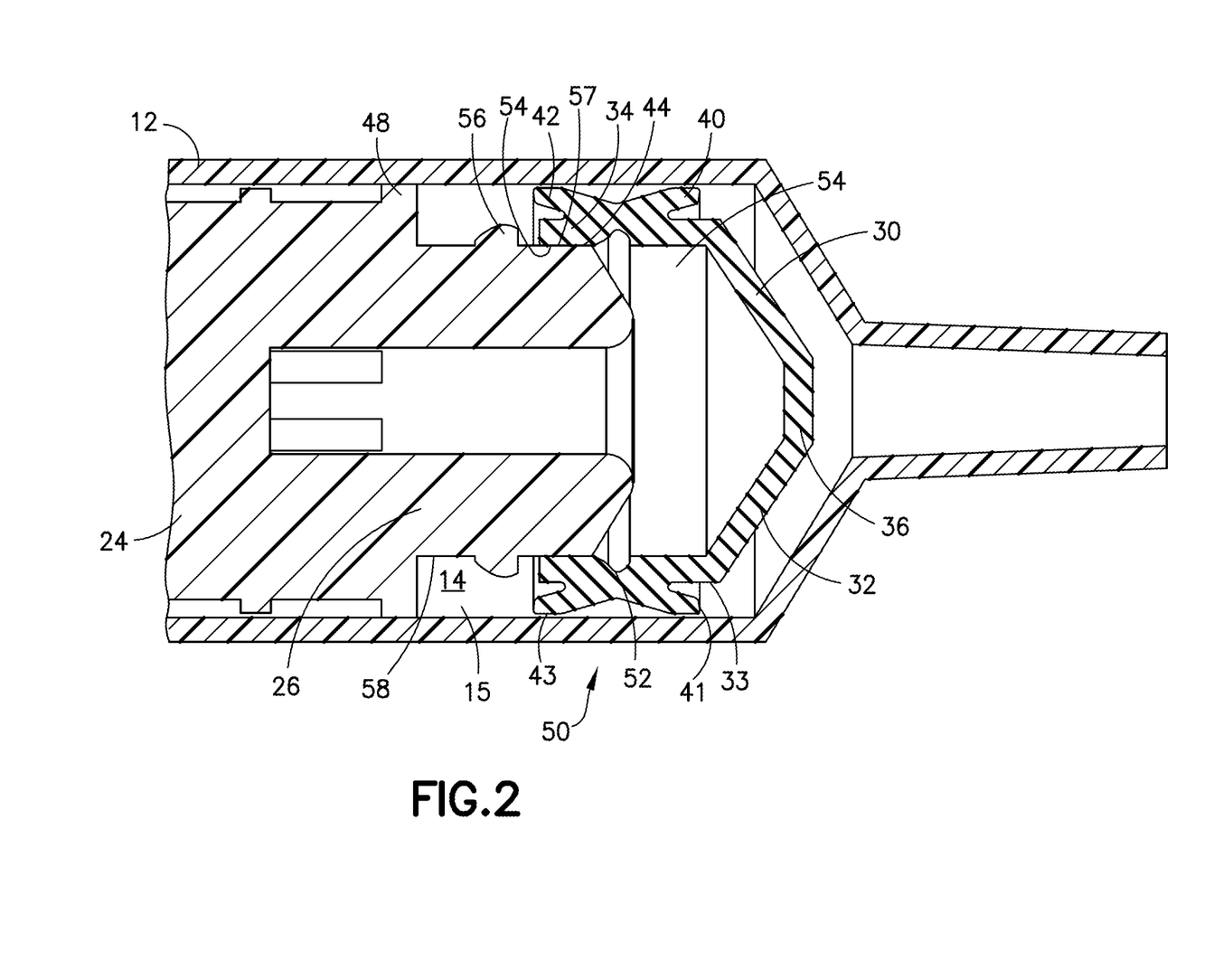
FIG. 2 is a cross-sectional view of the time-of-use activated syringe assembly of FIG. 1 in a pre-loaded condition in accordance with an embodiment of the present invention.
Figure 3:
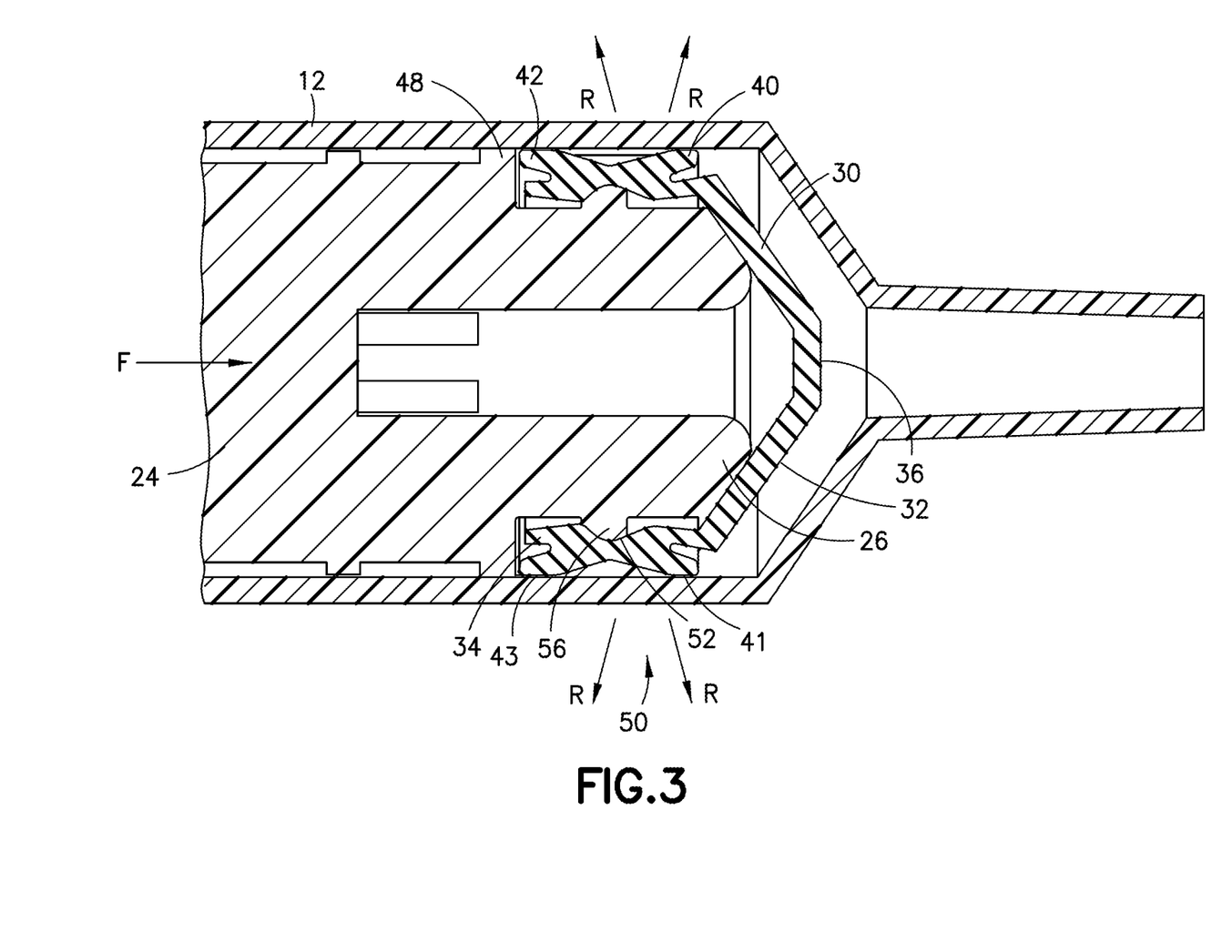
FIG. 3 is a cross-sectional view of the time-of-use activated syringe assembly of FIG. 2 in an activated condition in accordance with an embodiment of the present invention.

FIGS. 2 and 3 show side cross-sectional views of the time-of-use activated stopper 30 in accordance with an embodiment of the invention. The stopper 30 includes a first perimetrical skirt 40 extending around an outer circumference 33 of the main body 32 toward the closed front end 36 of the main body portion 32. The primary purpose of the first perimetrical skirt 40 is to provide an "active seal" between the stopper body and an inner wall 15 of the syringe barrel 12. The first perimetrical skirt 40 can have a thickness from about 0.05 nm to about 3 mm, and desirably a thickness of about 0.2 mm to about 0.5 mm. The length of the first perimetrical skirt 40 may be about 1 mm to about 10 mm. In addition, the first perimetrical skirt 40 includes a tip 41 that comes in contact with the inner wall 15 of the syringe barrel 12. The tip 41 may have any variety of localized shapes, such as, but not limited to, round, angled, serrated, etc.

An activation mechanism, generally indicated as 50, is associated with at least one of the stopper 30 and the forward front attachment end 26 of the plunger rod 24. The plunger rod 24 is configured for transition between a pre-loaded position, as shown in FIG. 2 in which the activation mechanism 50 is unactivated, and a loaded, ready-to-use position, as shown in FIG. 3 in which the activation mechanism 50 is activated so that it applies a radial force to the first perimetrical skirt 40 causing the first perimetrical skirt 40 to expand in the radial direction "R" causing at least tip 41 to seal against the inner wall 15 of the syringe barrel 12.

With continuing reference to FIGS. 2 and 3, according to one design, the activation mechanism 50 can include a first engagement member 52 extending around an inner circumference 54 of the main body 32 of the stopper 30 and a second engagement member 56 extending around an outer circumference 58 of the forward front attachment end 26 of the plunger rod 24. The first and second engagement members 52, 56 become engaged with one another upon transition of the plunger rod 24 from the pre-loaded position, as shown in FIG. 2 to the loaded, ready-to-use position shown in FIG. 3. As shown in the Figures, the first engagement member 52 can be a notch and the second engagement member 56 can be a protrusion which corresponds in shape with the notch so that, when engaged, the notch receives the protrusion therein. It can be appreciated that the first engagement member 52, located on the main body 32 of the stopper 30 can be a protrusion and the second engagement 56, extending around the outer circumference 58 of the forward front attachment end 26 can be a notch. It also can be appreciated that the shape of the notch is not to be construed as limiting the present invention as other interfaces between the notch and the forward front attachment end 26 of the plunger rod 24, such as linear or curved interfaces, could be utilized to provide the same function. While the shape of the first engagement member 52 or notch is shown in the figures as having a substantially conical cross-section, this shape is not to be construed as limiting the present invention as any suitable shape may be utilized.

The open rearward end 34 of the stopper 30 is configured to cooperate with the forward front attachment end 26 of the plunger rod 24 to engage the forward front attachment end 26 of the plunger rod 24 in the pre-loaded position and to guide the forward front attachment end 26 of the plunger rod 24 into the stopper 30 during transition from the pre-loaded position, shown in FIG. 2 to the loaded position, shown in FIG. 3. For example, as shown in FIG. 2 at 44, a rearward portion of the inner circumference 54 of main body 32 of the stopper 30 can engage a forward portion 57 of the outer circumference 58 of the forward front attachment end 26 of the plunger rod 24.

The stopper can further include a second perimetrical skirt 42 extending around the outer circumference 33 of the main body 32 and toward the open rearward end 34 of the main body 32. The primary purpose of the second perimetrical skirt 42 is to provide stability to the stopper 30 in an axial direction and to prevent tilting of the stopper 30. In addition, when fluid pressure is decreased inside the syringe barrel 12 during an aspiration, the second perimetrical skirt 42 includes a tip 43 that is forced against the inner wall 15 of the syringe barrel 12, thereby providing a sealing pressure between the stopper 30 and the inner wall 15 of the syringe barrel 12. The second perimetrical skirt 42 can have a thickness from about 0.05 mm to about 3 mm, or even a thickness of about 0.2 nm to about 0.5 mm. The length of the second perimetrical skirt 42 may be about 1 mm to about 10 mm.

Activation of the activation mechanism 50 applies the radial force in the radial direction "R" to both the first and the second perimetrical skirts 40, 42 to cause at least the tips 41, 43 of the first and second perimetrical skirts 40, 42 to seal against the inner wall 15 of the syringe barrel 12.

The stopper 30 can be formed from a bio-based or partially bio-based polymer material. One example of a bio-based material that can be used to form the stopper 30 include Dupont™ RS Hytrel® RS thermoplastic elastomers. This thermoplastic elastomer contains 20-60% renewably sourced polyol derived from plant feedstocks. The durometer hardness of the materials forming the stopper are between Shore D 30-60. Shore D 30 is equivalent to a Shore A 90.

Although the available RS Hytrel® thermoplastic elastomers are harder than the stopper materials currently in use, these thermoplastic elastomers offer unique properties. In general, thermoplastic elastomers are a class of materials that combine strength/stiffness and flexibility/elasticity. Hytrel® materials have been used for applications requiring load bearing, flexing, sealing, shock absorption, or elastic recovery from deformation. Used in a thin section, Hytrel® can behave like rubber but in thicker sections, it functions similar to engineering plastics or metals. The stopper 30 of the present invention, formed from Hytrel® thermoplastic elastomers and including the first perimetrical skirt 40 and second perimetrical skirt 42, when compared with "2-ribbed" stopper designs, shows reduced seal compression, requires lower forces to move the stopper, and minimizes sticktion effects while maintaining adequate seal function.

The stopper material may also be formed from polyolefines (e.g., PE, PP, and their copolymers), polyamides (e.g., nylons), polyesters (e.g., PET), polystyrene, polyurethane, polycarbonate, acrylonitrile-butadiene-styrene, fluoropolymers, ionomers, polyacrylates, or any other similar material as long as the polymeric material is sufficiently "rigid" or "semi-rigid". Moreover, any bio-derived, biodegradable, and recycled polymer with the elastic modulus between about 0.01 and about 5 GPa may also be used with the stopper in accordance with the present invention. Since the stopper 30 is manufactured from a "rigid" or "semi-rigid" polymeric material, a significantly lower coefficient of friction and contact area/pressure relative to a conventional rubber stopper is provided. Accordingly, the stopper 30 can be used with a syringe assembly 10 without silicone oil or other lubricants. In addition, the syringe barrel 12 may be made of the same material or a similar material as the stopper 30.

Figure 4A:
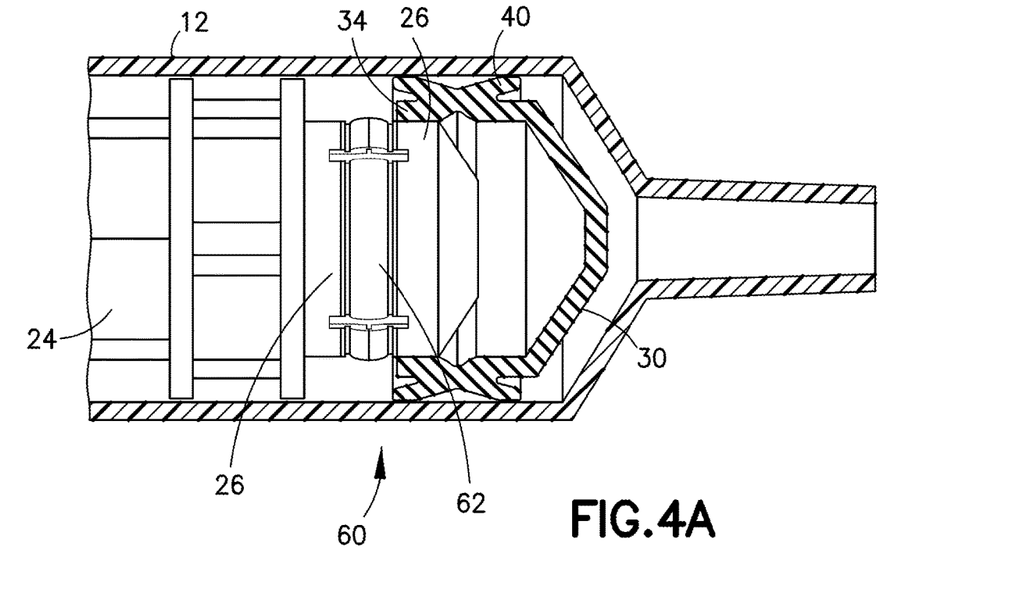
FIGS. 4A and 4B are cross-sectional views of the time-of-use activated syringe assembly of FIG. 1 in a pre-loaded and activated condition respectively, wherein the activation mechanism includes a flexing collet or basket associated with a front attachment end of a plunger rod in accordance with an embodiment of the present invention.
Figure 4B:
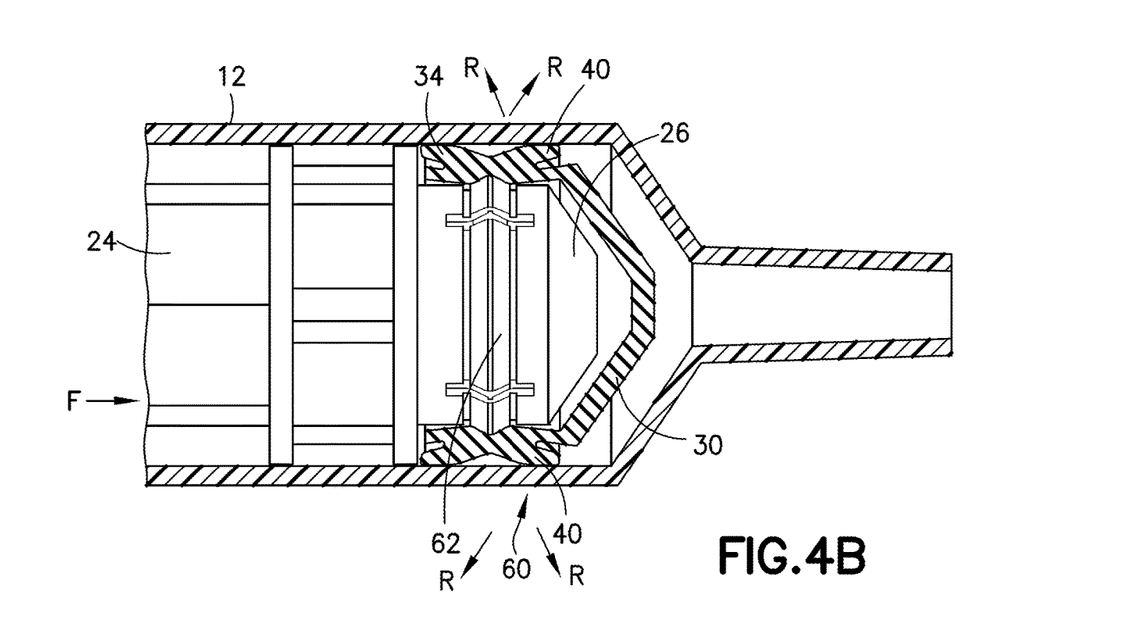

Reference is now made to FIGS. 4A and 4B, which show the activation mechanism, generally indicated as 60, according to another design of the invention. The activation mechanism 60 can include a flexing collet or basket 62 associated with the forward front attachment end 26 of the plunger rod 24. Upon transition of the plunger rod/stopper from the pre-loaded position shown in FIG. 4A to the ready-to-use position, shown in FIG. 4B, such as, when a force "F" is applied to the plunger rod 24 to cause the forward front attachment end 26 of the plunger rod 24 to enter through the open rearward end 34 of the stopper 30, the flexing collet or basket 62 expands and locks in place to apply the radial force "R" to the first perimetrical skirt 40.

Figure 5A:
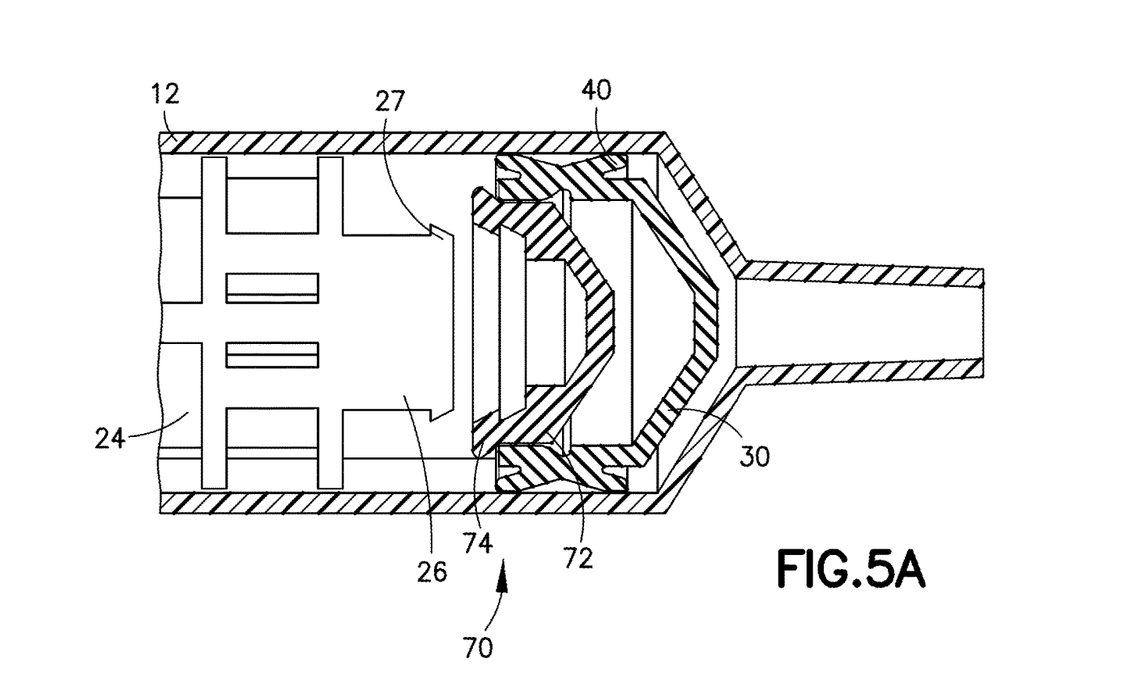
FIGS. 5A and 5B are cross-sectional views of the time-of-use activated syringe assembly of FIG. 1 in a pre-loaded and activated condition, respectively, wherein the activation mechanism includes a collapsing sliding wedge associated with the front attachment end of a plunger rod in accordance with an embodiment of the present invention.
Figure 5B:
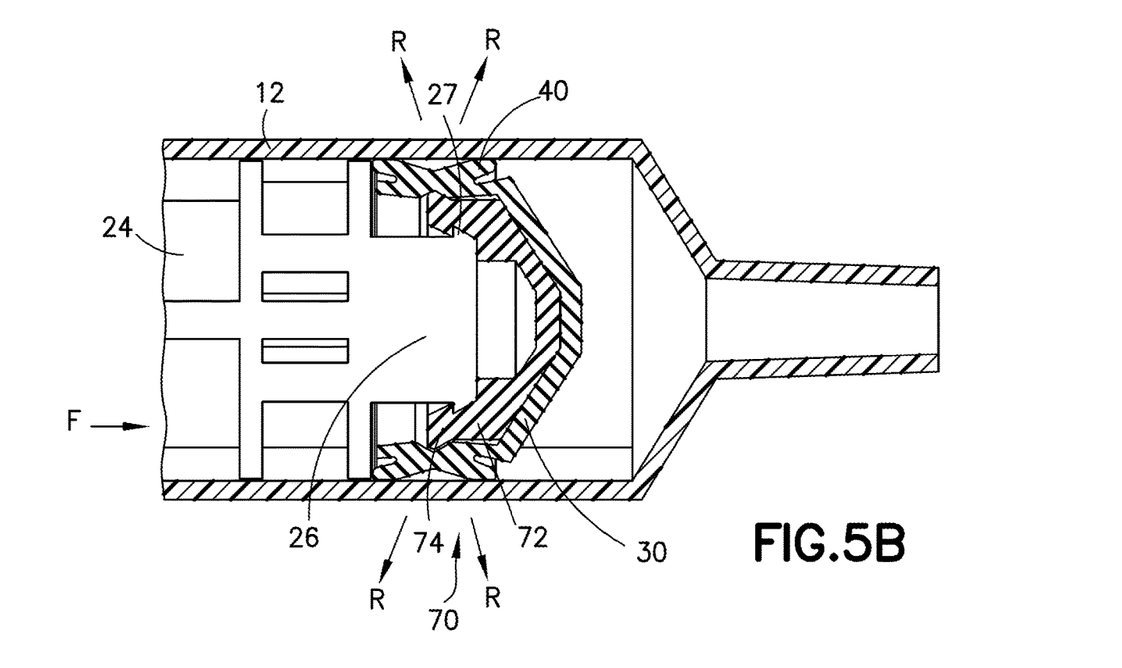

Reference is now made to FIGS. 5A and 5B, which show the activation mechanism, generally indicated as 70, according to still another embodiment of the invention. The activation mechanism 70 can include a collapsing sliding wedge 72 associated with the forward front attachment end 26 of the plunger rod 24, wherein the collapsing sliding wedge 72 is configured for expanding and locking in place to apply the radial force "R" to the first perimetrical skirt 40 upon transition of the plunger rod 24 from the pre-loaded position as shown in FIG. 5A to the loaded, ready-to-use position illustrated in FIG. 5B. It can be appreciated that the sliding wedge 72 can be configured to break away, slide, buckle, or move, as necessary to expand the stopper 30 in a radial direction "R".

The sliding wedge 72 can include an undercut portion 74 configured to cooperate with a protuberance 27 located at the distal end of the forward front attachment end 26 of the plunger rod 24 to lock the plunger rod 24 in place within the sliding wedge 72 and stopper 30 in the ready-to-use position shown in FIG. 5B.

Figure 6A:
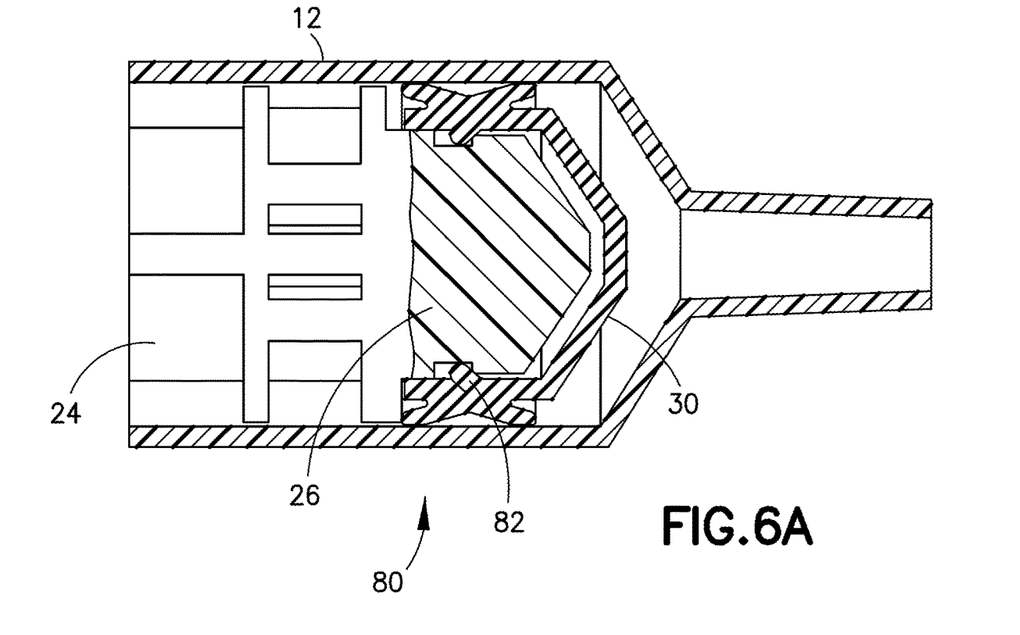
FIGS. 6A and 6B are cross-sectional views of the time-of-use activated syringe assembly of FIG. 1 in a pre-loaded and activated condition, respectively, wherein the activation mechanism includes a camming mechanism associated with the front attachment end of the plunger rod in accordance with an embodiment of the present invention.
Figure 6B:
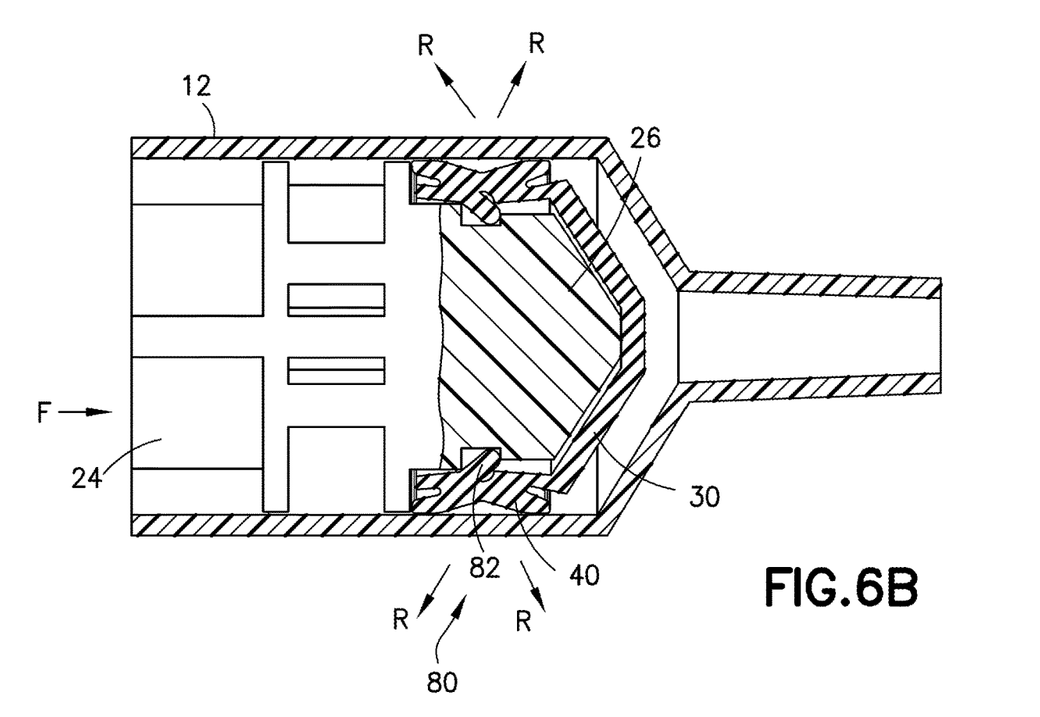

Reference is now made to FIGS. 6A and 6B, which show the activation mechanism 80, according to yet another embodiment of the invention. The activation mechanism can include a camming mechanism 82 associated with the stopper 30 and the forward front attachment end 26 of the plunger rod 24. Activation of the camming mechanism 82 applies the radial force "R" to the first perimetrical skirt 40 upon transition of the plunger rod 24 from the pre-loaded position as in FIG. 6A to the loaded, ready-to-use position shown in FIG. 6B. As shown in FIG. 6B, application of force "F" to the plunger rod 24 causes the camming mechanism to pivot from a rearward or proximal facing direction to a forward or distal facing direction.

Referring back to FIGS. 1, 2, and 3, a method of activating a time-of-use syringe assembly 10 includes providing a syringe barrel 12 defining an interior chamber 14, a proximal end 16, and a distal end 18 terminating in a tip 20 having an opening 22 extending therethrough. The method also includes providing a stopper 30 within the syringe barrel 12. The stopper has a main body 32 defining an open rearward end 34 and a closed front end 36. The stopper includes a first perimetrical skirt 40 extending around an outer circumference 33 of the main body 32 toward the closed front end 36 of the main body portion 32. The method further includes providing a plunger rod 24 having a forward front attachment end 26 and a back end 28 and extending along a longitudinal axis "L" and providing an activation mechanism 50 on at least one of the stopper 30 and the forward front attachment end 26 of the plunger rod 24. The method also includes associating the forward front attachment end 26 of the plunger rod 24 with one of the syringe barrel 12 and the open rearward end 34 of the stopper 30 in a pre-loaded position, and transitioning the plunger rod 24 from the pre-loaded position in which the activation mechanism 50 is unactivated to a loaded, ready-to-use position in which the activation mechanism 50 is activated and applies a radial force in a radial direction "R" to the first perimetrical skirt 40 causing the first perimetrical skirt 40 to seal against the inner wall 15 of the syringe barrel.

Transitioning of the plunger rod 24 from the pre-loaded position to the loaded, ready-to-use position includes applying a force "F" to the plunger rod 24 to cause the forward front attachment end 26 of the plunger rod 24 to enter into the open rearward end 34 of the stopper 30. According to one embodiment, the force "F" applied to the plunger rod 24 can be a distally directed force. The method can further include providing a retaining ring 46 at the proximal end 16 of the syringe barrel 12 extending toward the interior chamber 14 of the syringe barrel 12 and providing a stop member, such as in the form of a disk 48, on the plunger rod 24. The stop member or disk 48 can be located proximal to the stopper 30. The retaining ring 46 and the stop member or disk 48 are configured to cooperate together to prevent the plunger rod 24 from inadvertently separating from the syringe barrel 12 when the plunger rod 24 is in the pre-loaded position.

As previously stated, conventional syringe systems are designed with the stopper outer diameter/barrel inner diameter interface having significant interferences. This degree of interference is needed to create and maintain an adequate fluid/air seal for functional filling and injection operations over the entire intended shelf-life of the system. However, this type of interface can result in high compression/deformation of the stopper and barrel, and high contact forces of the stopper against the inner wall of the barrel, both of which can lead to undesired effects. These effects include compression set of cold flow of the stopper and the barrel where the outer diameter of the stopper or wall of the barrel takes a permanent deformation and the effective seal between the stopper and barrel is lost.

The time-of-use activated syringe assembly of the present disclosure overcomes many disadvantages of conventional syringe systems, as the stopper and barrel are assembled and staged in an unstressed/unstrained state during shelf-life. The design of the present disclosure enables the use of syringe stopper and barrel materials that have properties and/or geometries that require no or low stresses/strains during shelf-life storage. Higher durometer or more rigid elastomeric/plastic stoppers and thinner wall-section syringe barrels can be utilized resulting in more possibilities for alternative design geometries, overall reduced material weight, and cost. The sealing function of the stopper against the barrel inner diameter is engaged "on-demand" by the user immediately prior to use. The sealing performance of the stopper/barrel interface is improved because the components do not have a previous stress/strain "history" from being stored for an extended duration with components under high interferences. Long term effects of compression set (loss of resiliency) and effects of creep (dimensional change) that occur in a conventional syringe system with plastic/elastomer component materials are minimized or avoided. The plunger rod can be packaged inside the syringe assembly. Also, training of medical personnel to perform the required activation step would be relatively easy as medical personnel are already trained to "exercise" the syringe prior to use. Further, the steps to draw up a medicament require that the plunger be fully pressed to exhaust the air from the syringe before withdrawing a dose.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the claims appended and any and all equivalents thereof.

The invention claimed is:

1. A stopper adapted for attachment with a plunger rod for use within a syringe barrel, the stopper comprising:
   (a) a main body defining an open rearward end and a closed front end, said open rearward end adapted to receive a forward front attachment end of such plunger rod;
   (b) a first perimetrical skirt extending around an outer circumference of the main body toward the closed front end of the main body portion;
   (c) a second perimetrical skirt extending around the outer circumference of the main body toward the open rearward end of the main body; and
   (d) an activation mechanism associated with at least one of the stopper and such plunger rod, wherein such plunger rod is configured for transition between a pre-loaded position in which the activation mechanism is unactivated and a loaded, ready-to-use position in which the activation mechanism is activated and applies a radial force to the first perimetrical skirt and the second perimetrical skirt causing the first perimetrical skirt and the second perimetrical skirt to seal against an inner wall of the syringe barrel,
   wherein the activation mechanism comprises a flexing collet or basket associated with the plunger rod, said flexing collet or basket configured for expanding and locking in place to apply the radial force to the first perimetrical skirt and the second perimetrical skirt upon transition of the plunger rod from the pre-loaded position to the loaded, ready-to-use position.

2. The stopper of claim 1, wherein the activation mechanism comprises a first engagement member extending around an inner circumference of the main body and a second engagement member extending around an outer circumference of the forward front attachment end of such plunger rod, wherein said first and second engagement members become engaged with one another upon transition of the plunger rod from the pre-loaded position to the loaded, ready-to-use position.

3. The stopper of claim 2, wherein the first engagement member comprises a notch and the second engagement member comprises a protrusion.

4. The stopper of claim 2, wherein the first engagement member comprises a protrusion and the second engagement member comprises a notch.

5. The stopper of claim 1, wherein the stopper is formed from a bio-based or partial bio-based polymer material.

6. The stopper of claim 1, wherein the stopper has a durometer of hardness between Shore D 30-60.

7. The stopper of claim 1, wherein the open rearward end of the main body of the stopper is configured to cooperate with the forward front attachment end of the plunger rod to engage the forward front attachment end of the plunger rod in the pre-loaded position and to guide the forward front attachment end of the plunger rod into the stopper during transition from the pre-loaded position to the loaded position.

8. A plunger rod and stopper assembly adapted for use with a syringe barrel, said assembly comprising:
   (a) a plunger rod having a forward front attachment end and a back end and extending along a longitudinal axis;
   (b) a stopper having a main body defining an open rearward end and a closed front end, said open rearward end adapted to receive the forward front attachment end of the plunger rod, said stopper including a first perimetrical skirt extending around an outer circumference of the main body toward the closed front end of the main body, and said stopper including a second perimetrical skirt extending around the outer circumference of the main body toward the open rearward end of the main body; and
   (c) an activation mechanism associated with at least one of the stopper and the plunger rod, wherein the plunger rod is configured for transition between a pre-loaded position in which the activation mechanism is unactivated and a loaded, ready-to-use position in which the activation mechanism is activated and applies a radial force to the first perimetrical skirt and the second perimetrical skirt causing the first perimetrical skirt and the second perimetrical skirt to seal against an inner wall of the syringe barrel,
   wherein the activation mechanism comprises a flexing collet or basket associated with the plunger rod, said flexing collet or basket configured for expanding and locking in place to apply the radial force to the first perimetrical skirt and the second perimetrical skirt upon transition of the plunger rod from the pre-loaded position to the loaded, ready-to-use position.

9. The assembly of claim 8, further comprising a first engagement member having one of a notch or a protrusion and a second engagement member having the opposite of a notch or a protrusion.

10. A time-of-use activated syringe assembly comprising:
   (a) a syringe barrel defining an interior chamber, a proximal end, and a distal end terminating in a tip having an opening extending therethrough;
   (b) a plunger rod having a forward front attachment end and a back end and extending along a longitudinal axis, said forward front attachment end being located within the interior chamber of the syringe barrel;
   (c) a stopper located within the interior chamber of the syringe barrel, the stopper having a main body defining an open rearward end and a closed front end, said open rearward end adapted to receive the forward front attachment end of the plunger rod, said stopper including a first perimetrical skirt extending around an outer circumference of the main body toward the closed front end of the main body, and said stopper including a second perimetrical skirt extending around the outer circumference of the main body toward the open rearward end of the main body; and
   (d) an activation mechanism associated with at least one of the stopper and the plunger rod, wherein the plunger rod is configured for transition between a pre-loaded position in which the activation mechanism is unactivated and a loaded, ready-to-use position in which the activation mechanism is activated and applies a radial force to the first perimetrical skirt and the second perimetrical skirt causing the first perimetrical skirt and the second perimetrical skirt to seal against an inner wall of the syringe barrel, wherein the activation mechanism comprises a flexing collet or basket associated with the plunger rod, said flexing collet or basket configured for expanding and locking in place to apply the radial force to the first perimetrical skirt and the second perimetrical skirt upon transition of the plunger rod from the pre-loaded position to the loaded, ready-to-use position.

11. The assembly of claim 10, wherein the open rearward end of the stopper is configured to cooperate with the forward front attachment end of the plunger rod to engage the forward front attachment end of the plunger rod in the pre-loaded position and to guide the forward front attachment end of the plunger rod into the stopper during transition from the pre-loaded position to the loaded position.

12. The assembly of claim 10, including a retaining ring at the proximal end of the syringe barrel extending toward the interior chamber of the syringe barrel and a stop member associated with the plunger rod, the stop member being located proximal to the stopper and wherein the retaining ring and the stop member cooperate together to prevent the plunger rod from inadvertently separating from the syringe barrel.

13. A method of activating a stopper within a syringe barrel comprising:
(a) providing the stopper within the syringe barrel, the stopper having a main body defining an open rearward end and a closed front end, the stopper including a first perimetrical skirt extending around an outer circumference of the main body toward the closed front end of the main body, and the stopper including a second perimetrical skirt extending around the outer circumference of the main body toward the open rearward end of the main body;
(b) providing a plunger rod having a forward front attachment end and a back end and extending along a longitudinal axis;
(c) providing an activation mechanism on at least one of the stopper and the plunger rod;
(d) associating the forward front attachment end of the plunger rod with one of the syringe barrel and the open rearward end of the main body of the stopper in a pre-loaded position; and
(e) transitioning the plunger rod from the pre-loaded position in which the activation mechanism is unactivated to a loaded, ready-to-use position in which the activation mechanism is activated and applies a radial force to the first perimetrical skirt and the second perimetrical skirt causing the first perimetrical skirt and the second perimetrical skirt to seal against an inner wall of the syringe barrel.

14. The method of claim 13, wherein transitioning of the plunger rod from the pre-loaded position to the loaded, ready-to-use position includes applying a force to the plunger rod to cause the forward front attachment end of the plunger rod to enter into the open rearward end of the stopper.

15. The method of claim 14, wherein the force applied to the plunger rod comprises a distally directed force.

16. A method of activating a time-of-use syringe assembly comprising:
(a) providing a syringe barrel defining an interior chamber, a proximal end, and a distal end terminating in a tip having an opening extending therethrough;
(b) providing a stopper within the syringe barrel, the stopper having a main body defining an open rearward end and a closed front end, the stopper including a first perimetrical skirt extending around an outer circumference of the main body toward the closed front end of the main body, and the stopper including a second perimetrical skirt extending around the outer circumference of the main body toward the open rearward end of the main body;
(c) providing a plunger rod having a forward front attachment end and a back end and extending along a longitudinal axis;
(d) providing an activation mechanism on at least one of the stopper and the plunger rod;
(e) associating the forward front attachment end of the plunger rod with one of the syringe barrel and the open rearward end of the main body of the stopper in a pre-loaded position; and
(f) transitioning the plunger rod from the pre-loaded position in which the activation mechanism is unactivated to a loaded, ready-to-use position in which the activation mechanism is activated and applies a radial force to the first perimetrical skirt and the second perimetrical skirt causing the first perimetrical skirt and the second perimetrical skirt to seal against an inner wall of the syringe barrel.

17. The method of claim 16, wherein transitioning of the plunger rod from the pre-loaded position to the loaded, ready-to-use position includes applying a force to the plunger rod to cause the forward front attachment end of the plunger rod to enter into the open rearward end of the main body of the stopper.

18. The method of claim 17, wherein the force applied to the plunger rod comprises a distally directed force.

19. The method of claim 16, including providing a retaining ring at the proximal end of the syringe barrel extending toward the interior chamber of the syringe barrel and providing a stop member on the plunger rod, the stop member being located proximal to the stopper and wherein the retaining ring and the stop member cooperate together to prevent the plunger rod from inadvertently separating from the syringe barrel when the plunger rod is in the pre-loaded position.

* * * * *